United States Patent [19]

Bolle

[11] Patent Number: 5,576,775
[45] Date of Patent: Nov. 19, 1996

[54] EYEGLASSES WITH CONTROLLED VENTILATION FRAME AND LENS

[75] Inventor: Maurice Bolle, Oyonnax, France

[73] Assignee: Etablissements Bolle S.n.c., Oyonnax, France

[21] Appl. No.: 488,950

[22] Filed: Jun. 9, 1995

[51] Int. Cl.⁶ .............................. G02C 11/08; G02C 1/04; A61F 9/02
[52] U.S. Cl. .................................. 351/62; 351/106; 2/436
[58] Field of Search .................................. 351/83, 62, 85, 351/86, 90, 91, 93, 103, 105, 108, 106, 141, 158; 2/436, 445

[56] References Cited

U.S. PATENT DOCUMENTS

| | | | |
|---|---|---|---|
| 2,027,037 | 1/1936 | Gottieb | 351/62 |
| 2,444,498 | 7/1948 | Cochran | 351/86 |
| 2,513,507 | 7/1950 | Moeller | 351/86 |
| 2,529,068 | 11/1950 | Bernheim | 351/86 |
| 2,648,067 | 8/1953 | Parmelee | 351/86 |
| 3,233,249 | 2/1966 | Baratelli | 2/14 |
| 3,233,250 | 2/1966 | Jonassen | 2/14 |
| 3,517,393 | 6/1970 | Beauchef | 2/14 |
| 4,504,127 | 3/1985 | Cottet | 351/86 |
| 4,799,781 | 1/1989 | Weber | 351/86 |
| 4,951,322 | 8/1990 | Lin | 2/439 |
| 5,455,639 | 10/1995 | Magdelaine et al. | 351/106 |

*Primary Examiner*—Huy Mai
*Attorney, Agent, or Firm*—Carol W. Burton; Gregg I. Anderson; Holland & Hart LLP

[57] ABSTRACT

Eyeglasses are formed from a single curved lens and a frame supporting the lens along the upper edge thereof. A pair of temples are attached by hinges to the frame at the outer sides thereof. A central depending boss on the frame, a temple hinge boss at each outer side of the frame mounting the temple hinges, and depending supporting bosses intermediate the central boss and hinge bosses, each define a slot for receiving and retaining the upper edge of the lens. The boss slots being of a depth for supporting said lens with said upper edge thereof in spaced relation from said frame, fasteners securing said lens to said hinge bosses, and a fastener securing said lens to said central boss.

10 Claims, 3 Drawing Sheets

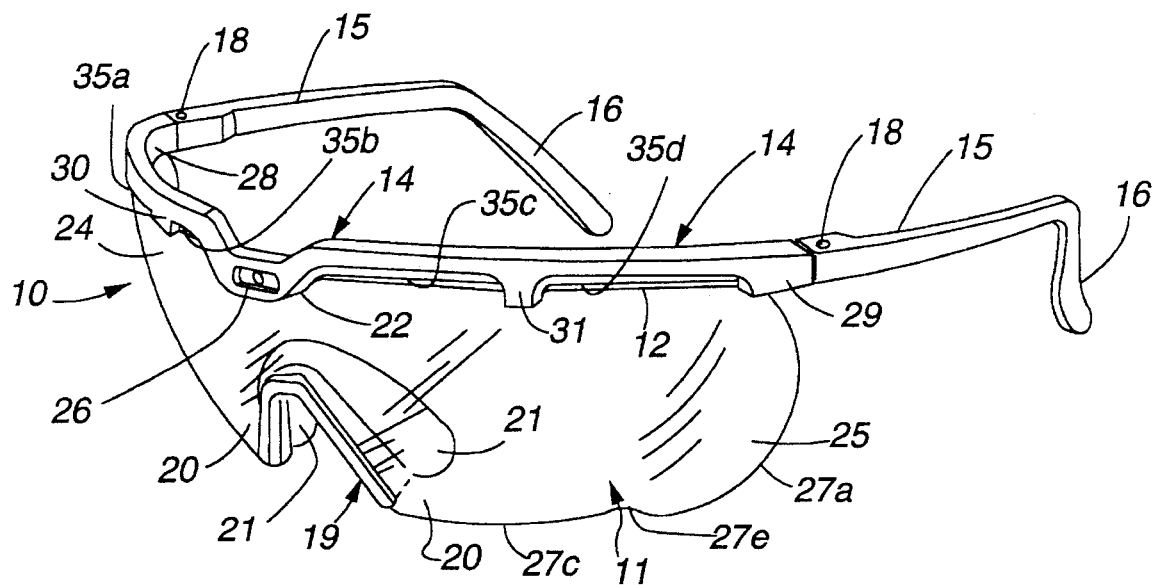
Fig. 1
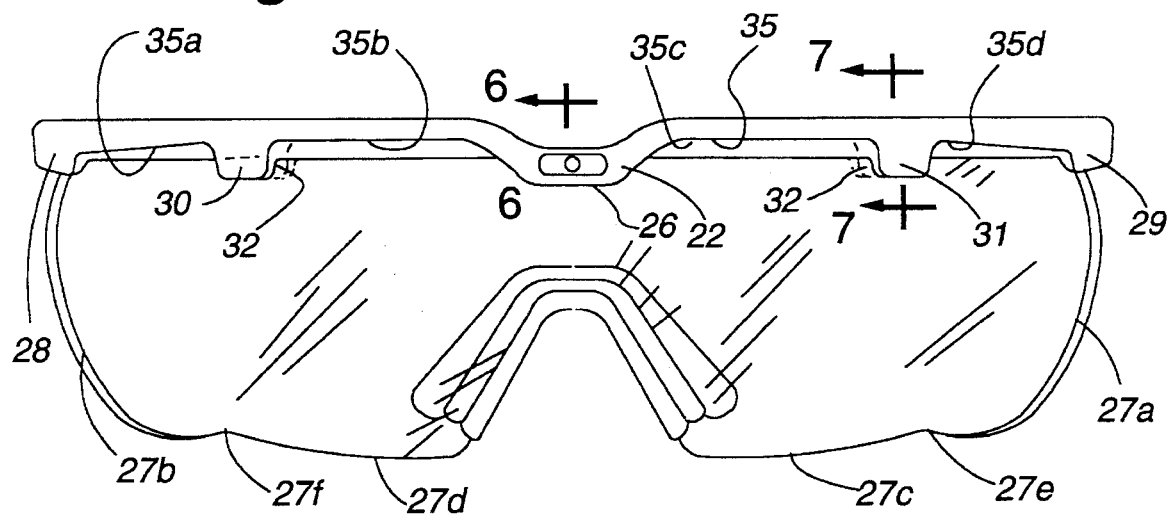
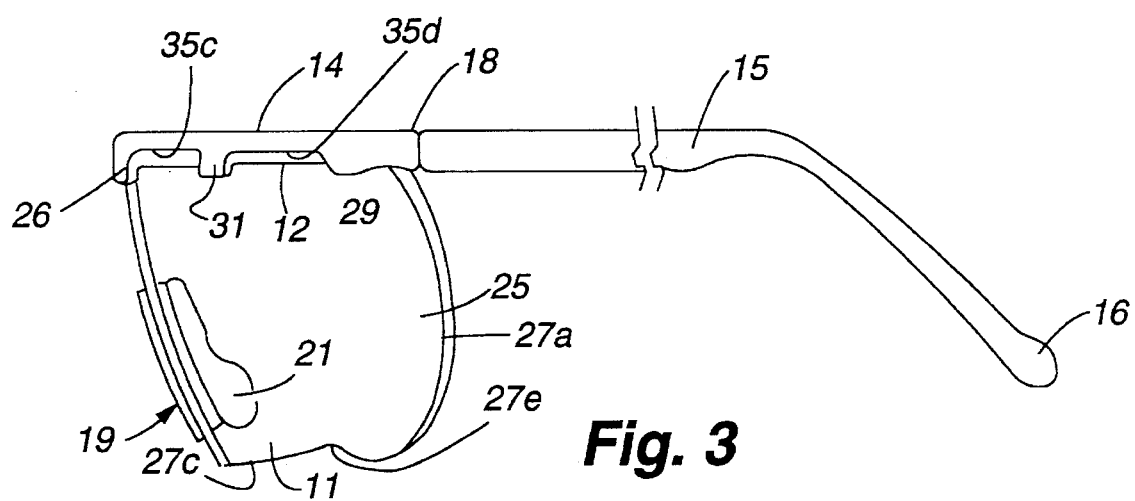
Fig. 3

5,576,775

EYEGLASSES WITH CONTROLLED VENTILATION FRAME AND LENS

BACKGROUND OF THE INVENTION

1. Field of the Invention

The present invention relates to eyeglasses and more particularly to eyeglasses with an improved frame providing ventilation between the frame and lens.

2. Description of the Prior Art

Eyeglasses which fit closely to a wearer's face tend to fog or cloud when used in cold weather or during exercise. Various frame structures have been utilized to prevent fogging in which the frame or bridge is spaced from the lens. See U.S. Pat. No. D347,017 and U.S. Pat. No. 4,425,669. One illustrative form of lens is shown in copending U.S. patent application Ser. No. 08/284,039, filed Aug. 1, 1994. The lens and nosepiece construction may also, for example, be of the character described and shown in U.S. Pat. No. 5,412,438.

OBJECTS OF THE INVENTION

The principal object of the present invention is to provide an improved frame construction for eyeglasses.

Another object is to provide an improved frame construction which reduces fogging and clouding of eyeglasses which fit closely on a wearer's face.

Other objects and advantages will become apparent from the following description and accompanying drawings.

SUMMARY OF THE INVENTION

Eyeglasses embodying the present invention comprise a single, unitary lens, a frame supporting the lens along the upper edge thereof, and temples hingedly attached to said frame at the outer sides thereof. A central depending boss on the frame, a hinge boss at each outer side of said frame mounting said temple hinges, and a depending supporting boss on said frame intermediate said central boss and each hinge boss, each of said bosses defining a slot for receiving and retaining the upper edge of said lens, said boss slots being of a depth for supporting said lens with said upper edge thereof in spaced relation from said frame, fasteners securing said lens to said hinge bosses, and a fastener securing said lens to said central boss.

DESCRIPTION OF THE DRAWINGS

FIG. 1 is a perspective view of eyeglasses embodying the present invention.

FIG. 2 is a front elevational view of the ventilated eyeglasses shown in FIG. 1.

FIG. 3 is a side elevational view of the eyeglasses shown in FIG. 1 the opposite side elevational view being a mirror image thereof.

DESCRIPTION OF THE PREFERRED EMBODIMENT

Figure 5:
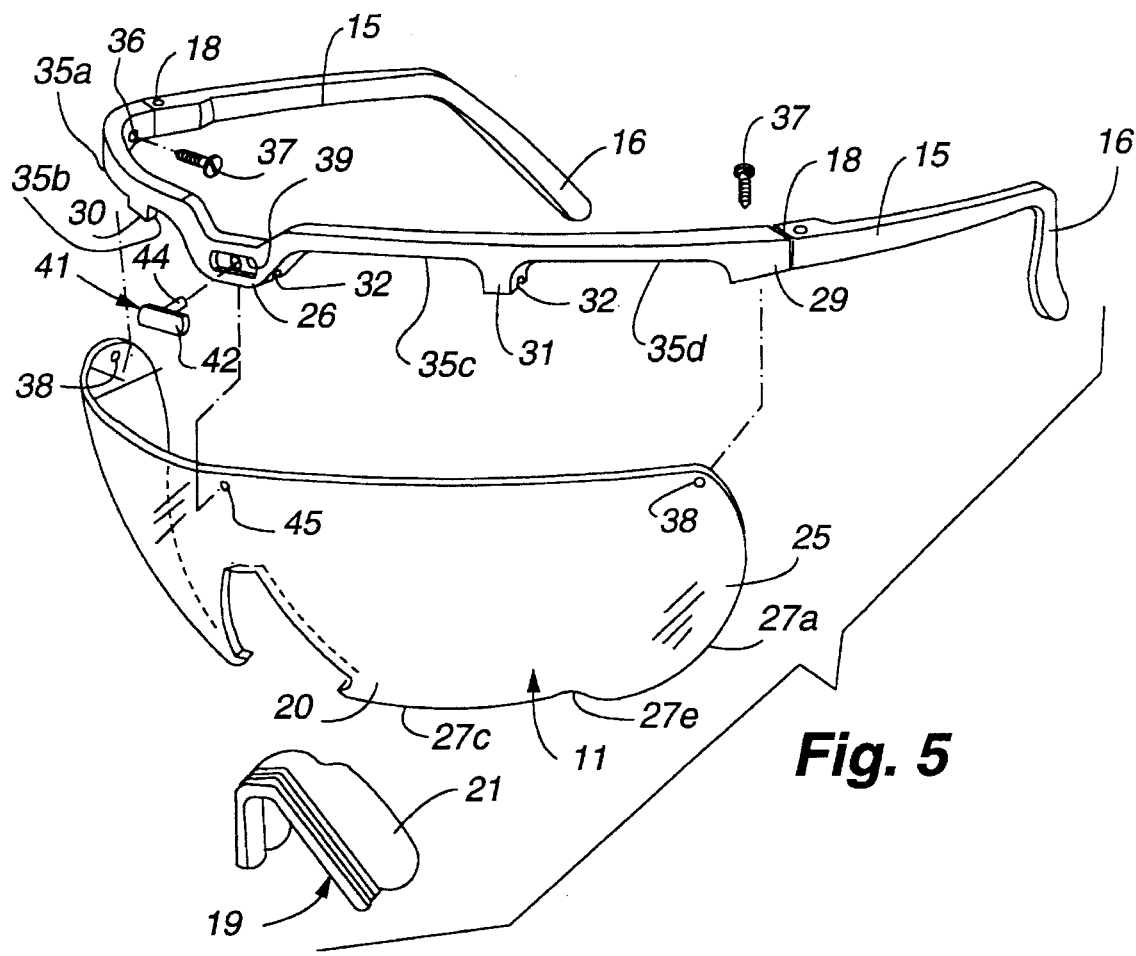
FIG. 5 is an exploded perspective view of the eyeglasses shown in FIG. 1.
Figure 4:
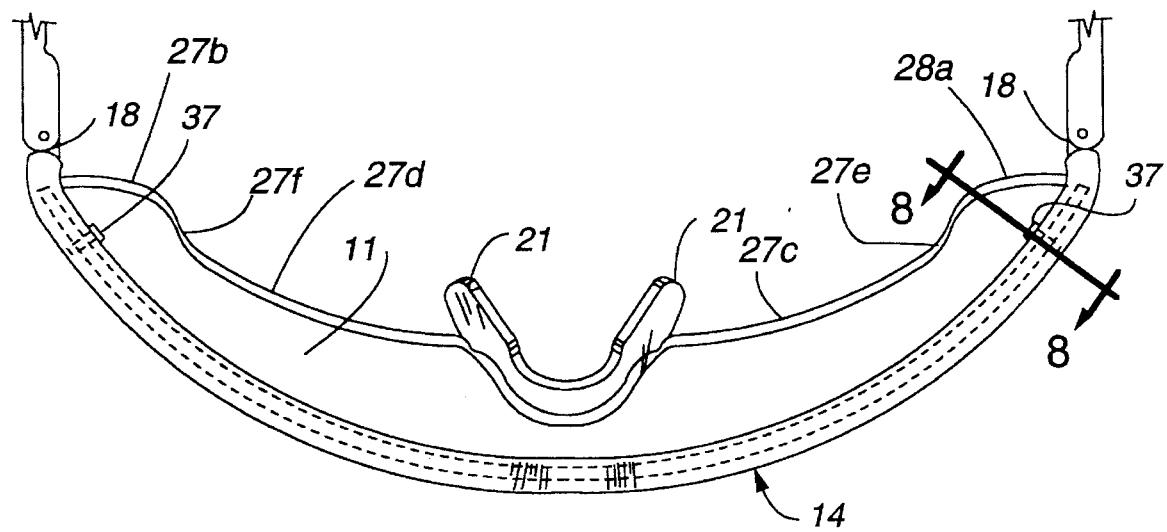
FIG. 4 is a top plan view of the eyeglasses shown in FIG. 1.

The present invention is embodied in eyeglasses 10 having a single, unitary, wrap-around lens 11 mounted at its upper edge 12 on a frame 14. Temples 15 having depending earpieces 16 are connected to the frame by hinges 18. A nosepiece 19 is attached to the lower edge portion 20 of the lens 11, and is formed with opposed nosepads 21. The lens 11 is secured to the frame 14 in spaced depending relation at a plurality of spaced apart connecting points beginning at the central portion 22 of the frame 14 and spaced outwardly toward the outer sides or ends 24, 25 of the lens 11. The lens may be of any convenient configuration such as flat, cylindrical, spherical or toroidal, or combinations thereof, forming a preferred wrap-around lens. In the preferred embodiment shown in FIGS. 1–5, the outer sides 24 and 25 of the lens 11 are defined by opposing outer arcuate edges 27a and 27b intersecting with opposing inner lens edges 27c and 27d at notches 27e and 27f of the lens 11. Inner lens edges 27c and 27d have a degree of curvature which is substantially less than the degree of curvature of the outer arcuate edges 27a and 27b, and as a result thereof, the unitary lens 11 curves around the upper face of the wearer, creating areas of differing pressures adjacent the notches 27e and 27f, which results in a ventilating air flow between the lens 11 and the face of the wearer.

For supporting the lens, the frame 14 is a generally elongated member having a central portion 22 extending below the plane of the frame to define a central generally rectangular mounting boss 26. The curvature of the frame corresponds to the curvature of the upper edge 12 of the lens. At each of its outer ends adjacent the hinges 18, the frame 14 is formed with a further depending hinge boss 28, 29 on which the hinges 18 are mounted and to which the lens is attached. For supporting the lens intermediate its ends the frame 14 is provided on each side of the center boss 26 with a depending intermediate mounting boss 30, 31. Each boss 26, 28, 29, 30, 31 is formed with a downwardly opening slot 32 for receiving and supporting the inserted upper edge 12 of the lens 11. The slots are of a depth sufficient to support the lens but limited to support the lens in a spaced relation from the frame 14 thereby defining spaced slots 34 between the upper edge 12 of the lens 11 and the lower edge or surface 35 of the frame 14 and extending between the respective lens mounting bosses 26, 28, 29, 30, 31. Lower surface 35 of frame 14 includes flat lower surface portions 35a, 35b, 35c and 35d which extend between hinge boss 28 and adjacent intermediate mounting boss 30, between intermediate mounting boss 30 and central mounting boss 26, between central mounting boss 26 and intermediate mounting boss 31, and between intermediate mounting boss 31 and hinge boss 29, respectively. Slots 32 are medially formed in said bosses 26, 30 and 31, effectively bisecting bosses 26, 30 and 31, and as a result, lens 11 depends downwardly from frame 14 with the front half of lower surface portions 35a, 35b, 35c and 35d of frame 14 extending over the outwardly facing surface of the lens 11 and the back half of lower surface portions 35a, 35b, 35c and 35d of frame 14 extending over the substantially rearwardly facing surface of lens 11.

Figure 8:
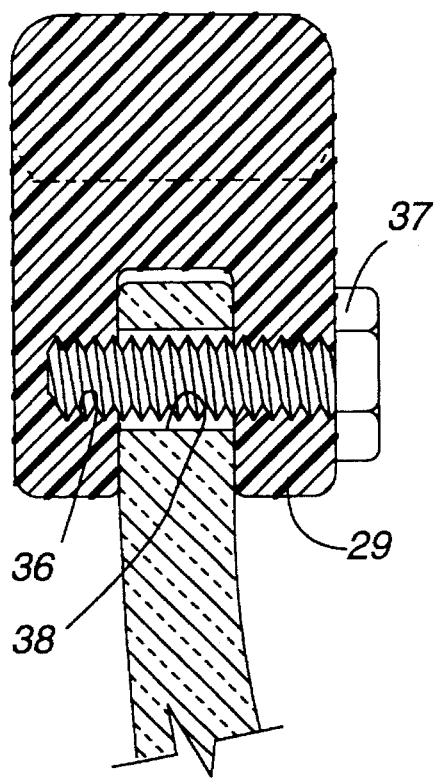
FIG. 8 is an enlarged section view taken substantially in the plane of line 8—8 on FIG. 4.
Figure 7:
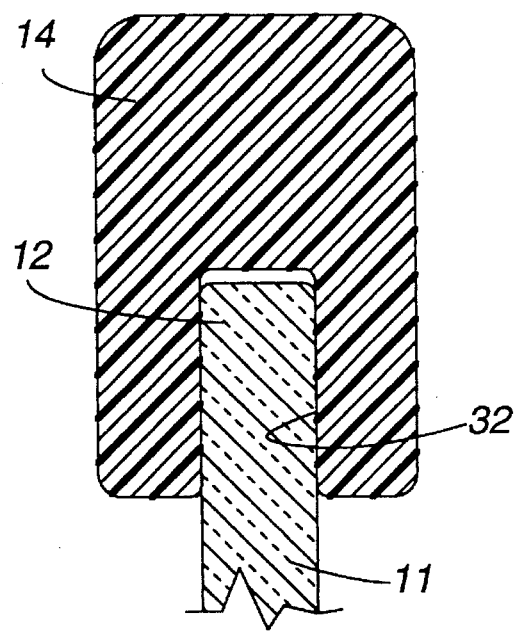
FIG. 7 is an enlarged section view taken substantially in the plane of line 7—7 on FIG. 2.
Figure 6:
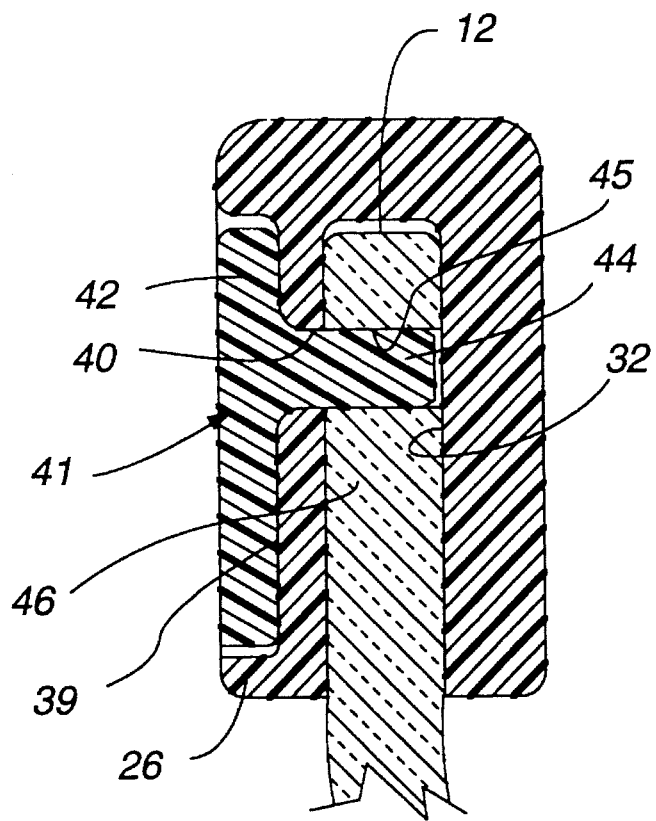
FIG. 6 is an enlarged section view taken substantially in the plane of line 6—6 on FIG. 2.

In order to secure the lens 11 to the frame 14, the hinge bosses 28, 29 are provided with threaded apertures 36 for receiving mounting screws 37 extending through the bosses and through appropriately defined apertures 38 in the upper edge portion 12 of the lens as shown in FIG. 8. At the central portion 22 of the frame 14, the center boss 26 is provided with an oblong recess 39, and an aperture 40 opening into the slot 32 and recess therein (FIG. 6). The recess 39 is closed by a T-shaped pin fastener 41 in the form of a plug having an oblong plate 42 with a rearwardly extending pin 44, adapted to extend through the aperture 40 and a corresponding aperture 45 in the upper central portion 46 of the lens 11 adjacent the edge 12 thereby securely fastening and supporting the lens 11 at its central portion as shown in FIG. 6.

While a certain illustrative embodiment of the present invention has been shown in the drawings and described above in detail, it should be understood that there is no intention to limit the invention to the specific form disclosed. On the contrary, the intention is to cover all modifications, alternative constructions, equivalents and uses falling within the spirit and scope of the invention as expressed in the appended claims.

I claim:

1. Eyeglasses comprising a single lens having a outwardly facing surface and an opposing and substantially rearwardly facing surface, a frame supporting said lens along the upper edge thereof, said frame having a front half, a back half, and a lower surface, temples hingedly attached to said frame at the outer sides thereof, a central depending boss on said frame, a hinge boss at each outer side of said frame mounting said temple hinges, and a depending supporting intermediate boss on said frame intermediate said central boss and each hinge boss, wherein said lower surface of said frame includes a plurality of flat lower surface portions spaced apart from said lens, one each said flat lower surface portions extending between adjacent each hinge bosses, intermediate bosses and said central depending boss, each of said bosses defining a medial slot effectively bisecting said bosses, for receiving and retaining the upper edge of said lens, said boss slots being of a depth for supporting said lens with said upper edge thereof in spaced relation from said frame, wherein said front half of said frame extends over said outwardly facing surface of said lens and said back half of said frame extends over said rearwardly facing surface of said lens.

2. The eyeglasses according to claim 1 wherein said outwardly facing surface of said lens is convex.

3. The eyeglasses according to claim 2 wherein said lens further comprises a pair of opposing outer arcuate edges having a first degree of curvature and a pair of opposing inner arcuate edges having a second degree of curvature, wherein said second degree of curvature is less than said first degree of curvature.

4. The eyeglasses according to claim 3 wherein said each of said outer arcuate edges intersects one of said inner arcuate edges at a notch formed in said lens.

5. Eyeglasses comprising a single lens, a frame supporting said lens along the upper edge thereof, temples hingedly attached to said frame at the outer sides thereof, a central depending boss on said frame, a hinge boss at each outer side of said frame mounting said temple hinges, a depending supporting boss on said frame intermediate said central boss and each hinge boss, each of said bosses defining a slot for receiving and retaining the upper edge of said lens, said boss slots being of a depth for supporting said lens with said upper edge thereof in spaced relation from said frame, fasteners securing said lens to said hinge bosses, and a fastener securing said lens to said central boss, wherein said lens includes a convex outwardly facing surface, an opposing concave and substantially rearwardly facing surface, a pair of opposing outer arcuate edges having a first degree of curvature and a pair of opposing inner arcuate edges having a second degree of curvature, wherein said second degree of curvature is less than said first degree of curvature.

6. The eyeglasses according to claim 5 wherein said each of said outer arcuate edges intersects one of said inner arcuate edges at a notch formed in said lens.

7. The eyeglasses according to claim 5 wherein the frame further comprises a front half, a back half, and a lower surface, wherein said lower surface of said frame includes a plurality of flat lower surface portions, one each extending between adjacent each hinge bosses, intermediate bosses and said central depending boss, wherein each said slot bisects one of said bosses and wherein said front half of said frame extends over said outwardly facing surface of said lens and said back half of said frame extends over said rearwardly facing surface of said lens.

8. Eyeglasses comprising a single wraparound lens having a plurality of lens apertures formed adjacent an upper edge of said lens, a frame supporting said lens along said upper edge thereof, temples hingedly attached to said frame at the outer sides thereof, a central depending boss on said frame, a hinge boss at each outer side of said frame mounting said temple hinges, a depending supporting intermediate boss on said frame intermediate said central boss and each hinge boss, each of said bosses defining a slot for receiving and retaining the upper edge of said lens, said boss slots being of a depth for supporting said lens with said upper edge thereof in spaced relation from said frame, threaded fasteners securing said lens to said hinge bosses, and a pin fastener securing said lens to said central boss, wherein said frame includes a front half, a back half, and a lower surface, said lower surface of said frame having a plurality of flat lower surface portions in spaced relation to said lens, one each extending between adjacent each hinge bosses, intermediate bosses and said central depending boss, wherein each said slot bisects one of said bosses and wherein said front half of said frame extends over said outwardly facing surface of said lens and said back half of said frame extends over said rearwardly facing surface of said lens.

9. The eyeglasses according to claim 8 wherein said lens further comprises a pair of opposing outer arcuate edges having a first degree of curvature and a pair of opposing inner arcuate edges having a second degree of curvature, wherein said second degree of curvature is less than said first degree of curvature.

10. The eyeglasses according to claim 9 wherein said each of said outer arcuate edges intersects one of said inner arcuate edges at a notch formed in said lens.

* * * * *